United States Patent [19]

Gatts

[11] 4,079,728

[45] Mar. 21, 1978

[54] PROGRAMMABLE INFANT CONTROLLED ENVIRONMENTAL TRANSITION SYSTEM

[76] Inventor: James D. Gatts, 2431 S. Dahlia La., Denver, Colo. 80222

[21] Appl. No.: 737,530

[22] Filed: Nov. 2, 1976

Related U.S. Application Data

[63] Continuation-in-part of Ser. No. 466,136, May 2, 1974, Pat. No. 3,993,042.

[51] Int. Cl.[2] ...................... A61B 19/00; A61G 11/00

[52] U.S. Cl. ..................................................... 128/1 B

[58] Field of Search ................. 128/1 R, 1 B, 1 C, 28; 5/61, 62

[56] References Cited

U.S. PATENT DOCUMENTS

| | | | |
|---|---|---|---|
| 1,943,888 | 1/1934 | Ewald | 5/62 X |
| 2,534,471 | 12/1950 | Norheim | 5/61 |
| 2,543,426 | 2/1951 | Terhaar | 128/1 B |
| 2,723,660 | 11/1955 | Greenberg | 128/1 R |
| 2,869,538 | 1/1959 | Hawk | 128/28 |
| 3,453,999 | 7/1969 | Neal | 128/1 R X |
| 3,809,065 | 5/1974 | Gatts | 128/1 R |

*Primary Examiner*—Dalton L. Truluck
*Attorney, Agent, or Firm*—Max L. Wymore

[57] ABSTRACT

The disclosed infant environmental transition system relates to the method and apparatus for providing an infant with an incrementally controlled, healthy transition from its intrauterine environment as it exists near birth to the extrauterine environment. The apparatus comprises a housing within which the infant is supported on a sling-like member. Means are provided to initially generate environmental conditions within the housing simulating the intrauterine environment and to alter this environment in controlled incremental steps to a normal extrauterine environment and in addition, means to allow the infant limited and selective control over certain features of his or her environment. Said means provide and control the tactile sensations perceived by the infant; the temperature and humidity within the container; the degree of movement imparted to the housing, which in turn is imparted to the infant; the degree of light perceived by the infant; and an audio profile which initially simulates intrauterine cardiovascular and gastro-intestinal sounds and gradually transitions to normal extrauterine sounds.

39 Claims, 10 Drawing Figures

PROGRAMMABLE INFANT CONTROLLED ENVIRONMENTAL TRANSITION SYSTEM

BACKGROUND OF THE DISCLOSURE

This application is a continuation-in-part of U.S. Application Ser. No. 466,136, filed May 2, 1974, now U.S. Pat. No. 3,993,042 issued Nov. 23, 1976.

Animals have the capability of adapting to many and various environmental conditions; the limitation of adaptation depends mainly on the animals's absolute physiological limitations and the rate of environmental change or adaptive pressure to which the animal is subjected. Successful adaptation to a new environment is frequently based on adequate previous learning or adaptation to environmental change. There are, inevitably, limits to the rate at which any animal can cope with environmental change. Exceeding these limits can result in a physiological breakdown (illness or death) and/or behavioristic reactions (inhibition or fear learning), which may program large areas of the infant's subsequent life. The adaptive capacity or capability can apparently always be extended or increased by an incremental or programmed change in the environment which is within the adaptive limits of the animal, and secondarily, by allowing the animal selective and limited control of its environment.

The most difficult transition that a mammal is required to make in its lifetime would appear to be the change from the intrauterine environment to the extrauterine environment at birth. Not only is every element of the infant's environment changed, but the effect (fear learning) is intensified because the animal has had no experience in adapting to changing environment conditions, as the intrauterine environment is highly protected by a number of mechanisms provided by nature.

The environmental changes through which an infant must transition include:

1. Temperature — The infant is maintained at body core temperature of 98.6° and transitions to delivery room temperature of approximately 70°. These figures may be modified by an increased maternal core temperaturee due to labor and evaporative cooling which the wet infant endures. The thermal shock of birth transition will range between 30° and 40° Fahrenheit.

2. Tactile sensation — An omni present, enclosing, mold, weightless, tactile sensation is present and applied equally over 100 percent of the infant's body. This sensation is generated by the uterus, the amniotic sac, and the hydraulic amniotic fluid system. In extrauterine life this tactile senation is changed to a pressure against small portions of the infants's head, trunk and legs estimated to be 15 percent to 20 percent of the body surface area. The weightlessness of counter balanced density in utero is changed to a feeling of heaviness as the infant is pressed by his own weight against a flat, comparatively hard, pad.

3. Audio — The term gravid intrauterine audio profile consists of a loud continuous din created mainly by maternal cardiovascular and gut sounds. The fluid sound transmission system present in the uterus is approximately five times as efficient as sound transmission in air. The extrauterine environment is strikingly different in audio patterns and in efficiency of transmission. Acoustic trauma can be induced by changing a long preconditioned sound pattern from loud to quiet equall as well as from quiet to loud.

4. Motion — The uterine enclosure moves frequently and smoothly in rolling movements above the fetus both day and night. The system is highly protective as pressures are transmitted through a hydraulic fluid equally to all portions of the infants's body. The infant is weightless and capable of free and easy movements within the container. In the extrauterine environment, the infant is pressed by his own weight, against the crib pad. His own movements are nearly impossible and the movement of the bassinet is completely foreign to anything he has experienced.

5. Light — The illumination level in the uterus is approximately zero. The infant is transitioned into an operating room illumination level of 200 to 300 foot lamberts of light energy.

Infant care, particularly immediately following birth, has evolved over the last several decades into a pattern which appears to be contrary to a healthy adaptation of the infant to its new environment. Most women in modern societies will give birth to their children in hospitals. To minimize microbiological contamination, hospital care is most often programmed for the newborn infant in such a way as to remove the infant from the mother and isolate it in a nursery. The nursery is frequently well lighted and kept at a temperature which is considerably less than the temperature the infant experiences in the intrauterine environment. In addition, the acoustic and tactile environment are grossly altered, as compared to the world the infant has known. Applicant is of the opinion that this abrupt change in the environment tends to intensify the infant's intrauterine to extrauterine transition and may create adaptive scars which affect the person's emotional and physical response to the subsequent adaptive or environmental changes throughout the remainder of his or her life.

The present invention has for one of its objects a method and apparatus which provides a gradual transition of an infant from its intrauterine environment to the extrauterine environment without requiring significant changes in the current method of handling and care of the infant and further provides means by which the infant can exercise limited and selective control of the environment to suit his or her wishes and desires.

Another object of the invention is to provide a new and improved infant environmental transition system which initially simulates parameters of the environment of the near term gravid uterus as the infant perceives them through bodily senses and permits the selective changing of said simulated parameters to parameters simulative of an extrauterine or other environment at a rate within the normal or nonpathological adaptive capacity of the infant and secondarily to grant the infant the additional advantages of control over certain limited features of his or her environment.

A further object of the present invention is to provide a new and improved infant environment transition system which initially simultes temperature, light, tactile sensation, motion and audio profile sensed by the infant in the near gravid uterus and gradually permits the change of these simulative parameters to simulate the extrauterine environment or an intermediate environment with features selected by the infant.

PREFERRED EMBODIMENT

These and other objects will become apparent to one skilled in the art in the following specification and drawings and in which.

Figure 1:
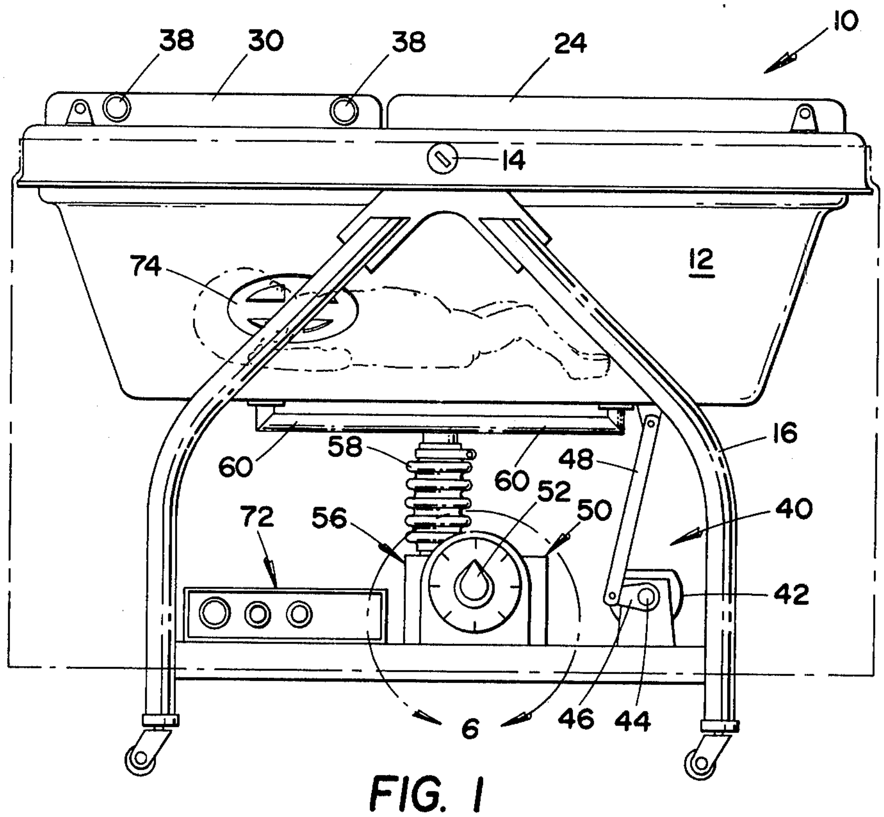
FIG. 1 is a side elevational view of the simulator according to the present invention.
Figure 2:
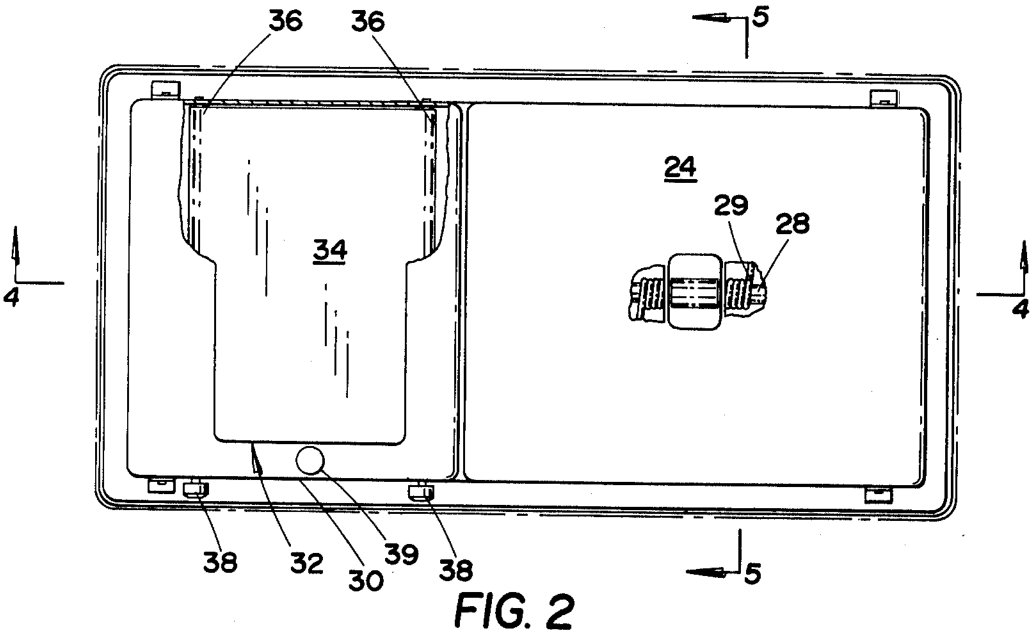
FIG. 2 is a plan view of the simulator of FIG. 1.
Figure 3:
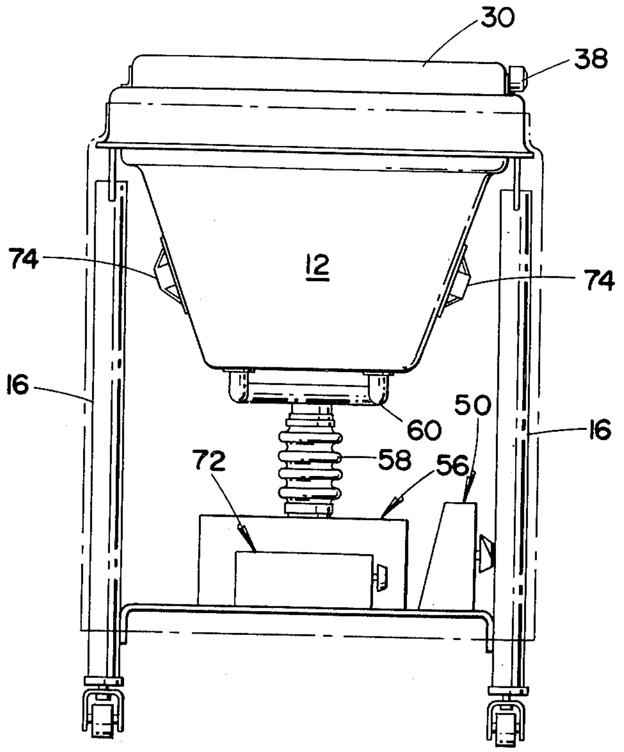
FIG. 3 is an end view of the simulator of FIG. 1.

Referring next to the drawings and initially to FIG. 1, an environmental system or simulator 10 is disclosed embodying the present invention. The simulator 10 provides for a gradual controlled transition for the infant from its intrauterine environment to the extrauterine or everyday environment to reduce the adaptive shock to the infant and permit a healthy adaptation. This transition is accomplished by system 10 reproducing initially, as nearly as practical, environmental parameters sensed by the infant just prior to birth such as body core temperature and humidity, audio profile, light, rocking motion, and tactile sensation. The system 10 gradually changes these parameters until the infant is exposed to parameters approximating the everyday environment.

The simulator 10 comprises a housing or container 12 adapted to receive the infant and which is supported by trunnions 14 on a frame 16. The housing 12 and frame 16 can be of various configurations as long as they contribute their respective functions to the simulator.

Figure 4:
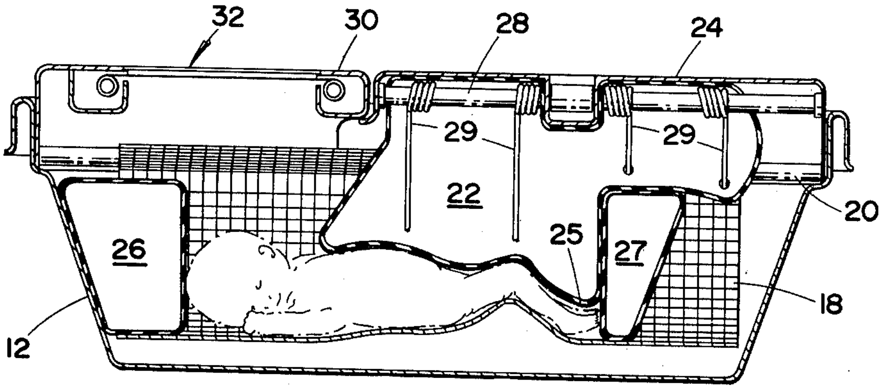
FIG. 4 is a sectional view of the simulator taken approximately along line 4—4 of FIG. 2.
Figure 5:
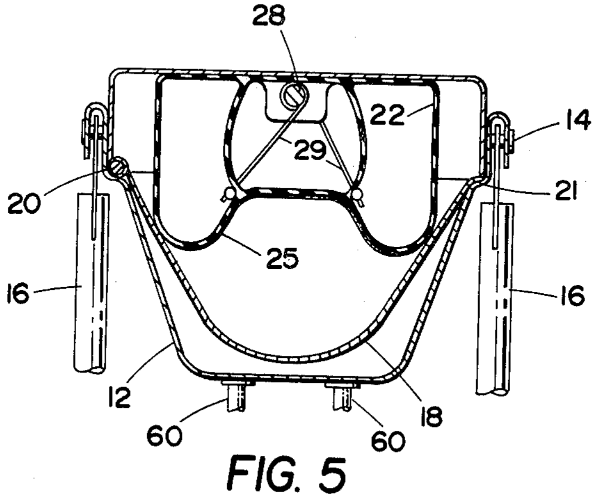
FIG. 5 is a sectional view taken approximately along line 5—5 of FIG. 2.
Figure 6:
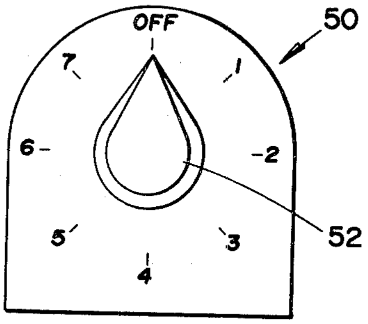
FIG. 6 is an elevational view illustrating an element of the simulator control encompassed by circle identified as 6 in FIG. 1 on an enlared scale.

The infant is supported in housing 12 by an adjustable sling 18 (FIGS. 4 and 5). Sling 18 is preferably of net-like or skeletal construction which is flexible to conform to the infant's body like a hammock. The infant can be placed on sling 18 with or without clothing. In the later case, the waste products generated by the infant can fall into an appropriate removable tray provided in the bottom of housing 12 through openings in the sling 18 if that feature is desirable.

The net-like sling construction also permits the controlled air to circulate around the infant's body while in the housing 12. The flexibility of the sling 18 permits the sling to conform to the infant's body and thus provide the tactile sensation to which the infant is accustomed while in the intrauterine environment.

The sling 18 is dependably supported in housing 12 by a rotatable rod-like support 20 on one side and fixed at 21 along the opposite side. The rod-like support 20 can be manually rotated to gradually take up one end of the sling until eventually the sling is a flat support similar to a mattress.

The tactile sensation is further enhanced by a fabric-covered low pressure pneumatic bladder 22 which is fitted to the underside of a pivoted cover 24 for the container 12. The base of the bladder may have a soft fabric layer 25 which when the bladder 22 is properly inflated exerts a very slight pressure against the infant, yet can easily be pushed away by the infant during exercise or movement. Head and foot pillows 26, 27 may be placed as shown in FIG. 4 which in combination with sling 18 and bladder 22 provide the infant with substantially encircling tactile sensation.

The bladder 22 is gradually taken up by rotating a rod 28 connected to bladder 22 by strings 29. Toward the end of the infant's stay in the simulator, the bladder 22 will be moved completely out of contact with the infant and can be removed from cover 24.

The infant is placed in and removed from the housing 12 through the pivoted cover 24. Cover 24 when raised moves bladder 22 out of the way so as not to interfere with placing or removing the infant from the simulator 10. A second pivoted cover 30 is provided and completes closure of the container 12.

When the baby is placed in sling 18 and covers 24 and 30 are closed, the simulaor 10 is substantially light tight to permit good control of the light admitted to the infant. Means 32 is provided in cover 30 to control the amount of admitted light. Means 32 may include a roll of decreasingly filtered flexible window material 34. The material 34 is connected at its ends to spools 36 supported in cover 30. Spools 36 can be rotated by knobs 38 to periodically change the degree of light admitted through material 34 by rolling same from one spool 36 to the other. A window 39 in cover 30 permits display of a numeral printed on the material 34 to indicate the portion of the filter material 34 that should be exposed for a particular period of age, for example, for the week of age of the infant. The material should filter light mainly from one side so that the infant can be easily viewed from outside the housing 12.

The simulator 10 incorporates means 40 (FIG. 1) for imparting a rocking motion to the housing 12 causing the housing 12 to pivot around trunnions 14. The motion imparting means 40 includes an electrical motor 42 which drives an output shaft 44 which is drivingly connected to the housing 12 through linkage 46, 48. When shaft 44 rotates in a clockwise direction as viewed in FIG. 1, motion is imparted to housing 12 through the links 46, 48 causing the housing 12 to go through a gentle rocking sequence. The motor 42 is controlled by control means 50.

Control means 50 is a timed control mechanism which is settable to close a circuit (not shown) periodically to impart the rocking motion according to a desired sequence. The control means 50 provides additional control functions which will be explained more fully hereafter. For purposes of controlling the motion imparting means 40, a selector 52 is set according to the age of the infant. When so set, control 50 will during the early weeks of birth effect actuation of motor 42 more frequently than at the end of the period of confinement. The selector may, for example, be advanced once each week, and the new setting will reduce the frequency of the rocking motion of housing 12 until finally there will be no rocking of the housing 12. The control 50 may include a general purpose microcomputer such as the Altair 8800 manufactured by MITS of Albuquerque, New Mexico, utilizing an Intel 8080A microprocessor and programmed to activate the environmental parameter generators of the system according to a limited and preselected program which may be managed by the infant. The computer programmer would provide for only limited and preselected changes in the areas wherein the infant could modify his or her own environment.

The air in housing 12 is initially controlled to provide a warm, moist environment similar in temperature to that experienced by the infant in the embryonic sac. Since the housing 12 is partially closed to ambient air, an air control means 56 is provided for generating and directing a source of air at proper temperature and humidity inot the bottom of housing 12 through a flexible hose 58 and manifold 60. The control means 56 can be any satisfactory commercially available unit which has the capability of varying the temperature and relative humidity of the air. An air cooler may be incorporated for very hot climates.

The integrated controller 50 also controlls the temperature and humidity of the air directed into the housing 12 through an electrical circuit (not shown). The air circulates within the housing 12 and is exhausted through suitable leakage designed into the housing 12. The temperature and humidity of the air is gradually reduced so that the last week the infant is in the simulator 10 the air will be approximately at or about ambient room conditions.

Figure 7:
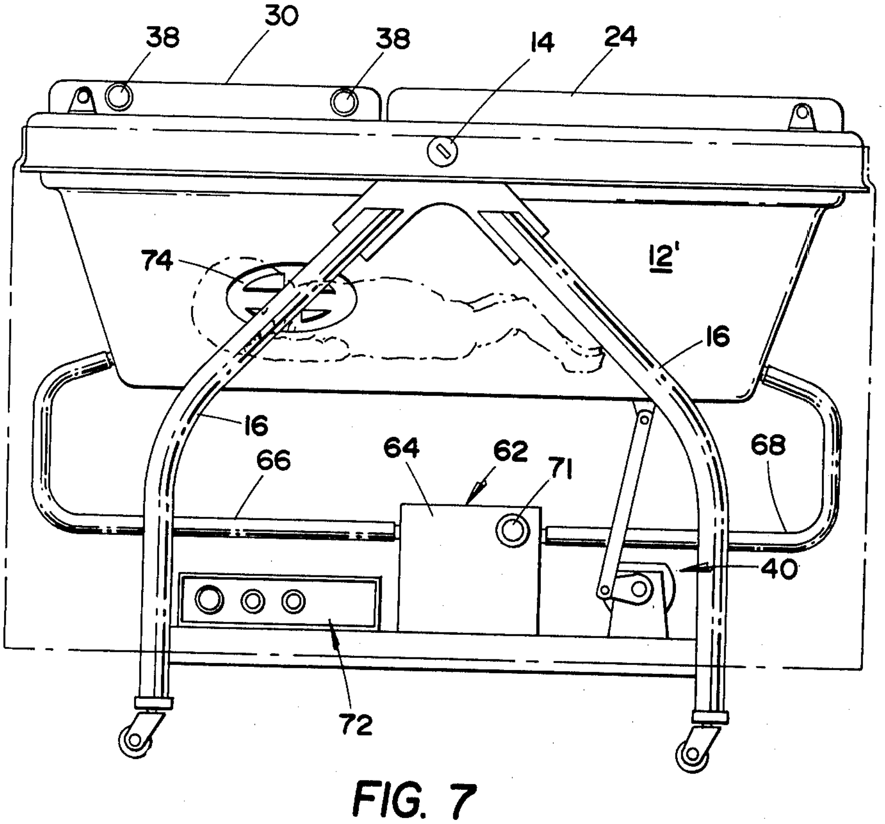
FIG. 7 is a view of the simulator similar to FIG. 1 but showing a modification thereto.
Figure 8:
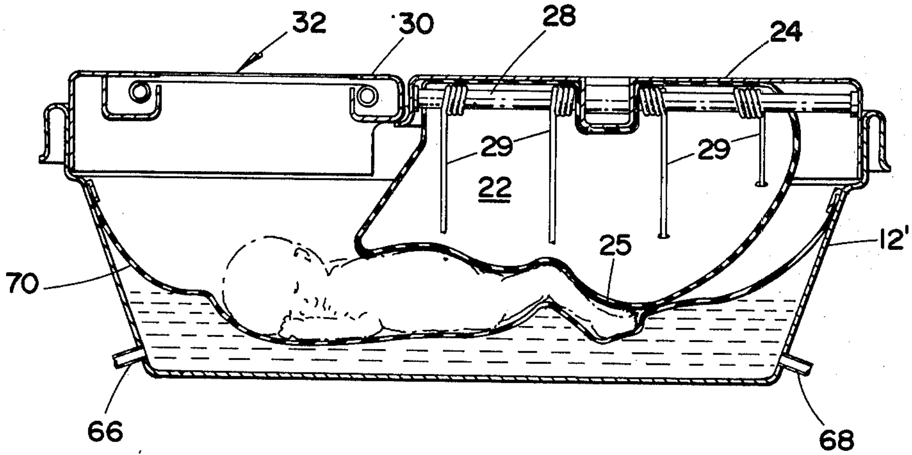
FIG. 8 is a view similar to FIG. 4 but further illustrates the modification of FIG. 7.
Figure 9:
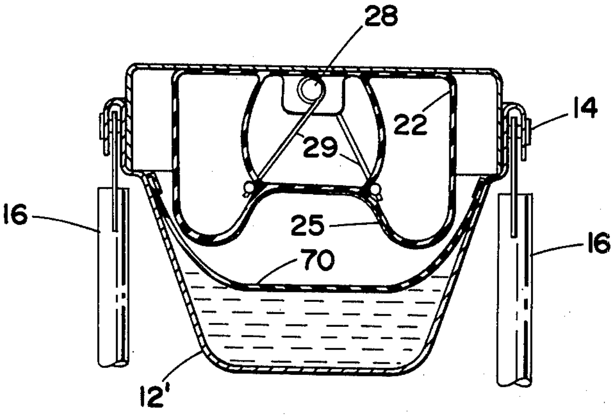
FIG. 9 is a view similar to FIG. 5 showing still further details of the modification disclosed in FIGS. 7 and 8; and, FIG. 10 is a block diagram of the switches, control circuitry, timers and parameter generators which will grant the infant limited and selective control of certain features of his or her environment.

FIGS. 7, 8 and 9 disclose a modified control means indicated generally as 62. Control means 62 includes a basic heating unit 64 which is controllable to heat and pumps water of varying temperatures through conduits 66 to the housing 12'. The control means 62 heats the water to a particular temperature and pumps through conduit 66 to a modified housing 12' best illustrated in FIG. 8. The water flows into the housing 12' and out the outlet 68 where it is returned to the pumping and heating unit 64.

The modified housing 12' includes a rubber sheet or the like 70 which forms a water tight barrier between the bottom of the housing 12' and the upper portion thereof into which the infant is placed. The water temperature is controlled initially at a higher temperature and gradually reduced to ambient temperature by setting the control knob 72. The infant is placed on the rubber sheet 70 and the temperature of the infant is controlled by the water circulating through the housing 12'.

The simulator 10 further includes means 72 for generating acoustical energy. Means 72 may comprise a radio, tape recorder, electronic signal generator, or similar controllable sound generating device. The audio content may comprise a variety of different simulated sounds or actual recordings of the noises present in the near term pregnant uterus or other sounds such as music or house sounds which may be generated electronically, put on tape, or played from a transmitter and reproduced in the housing 12. The acoustical means 72 directs the signal to speakers 74 suitably mounted on the sides of housing 12 and which direct the sound into the interior of the housing 12. The acoustic generator 62 can be suitably supported on a shelf provided on frame 16. The sound directed to the infant, like the other environment factors, will be gradually changed during tenancy of the infant from the intrauterine sounds to the outside world sounds under which the baby will be subjected. Later sounds can be, for example, ordinary day noise, music, etc.

The system may also incorporate an information system comprising a cardiophone or breath sensor mounted inside the simulator and connected to a remote speaker or alarm signal for the doctor or nurse to monitor.

A further object of the present invention is to provide for the infant's control over certain limited and selected aspects of the environment as soon as his or her maturity and physical development allows this to be accomplished.

There is evidence that the new born human infant feels overwhelmed and helpless to cope with the dramatic and adversive environmental change from interauterine to extrauterine life. The infant's own physical immaturity makes him or her a helpless victim of this chnge as the environment can only be modified by its mother or caretaker often on a schedule quite uncoordinated with its own needs or desires. Granting the infant the control over certain aspects of his or her environment would significantly modify this situation.

The infant controlled environment may appropriately comprise a series of transducers 100 such as switches 102–112 and the like positioned within housing 12 to be operated by the infant and which would in turn initiate the limited and preselected operation of or change in the environmental parameters within housing 12 for a predetermined limited or continuous period of time.

Figure 10:
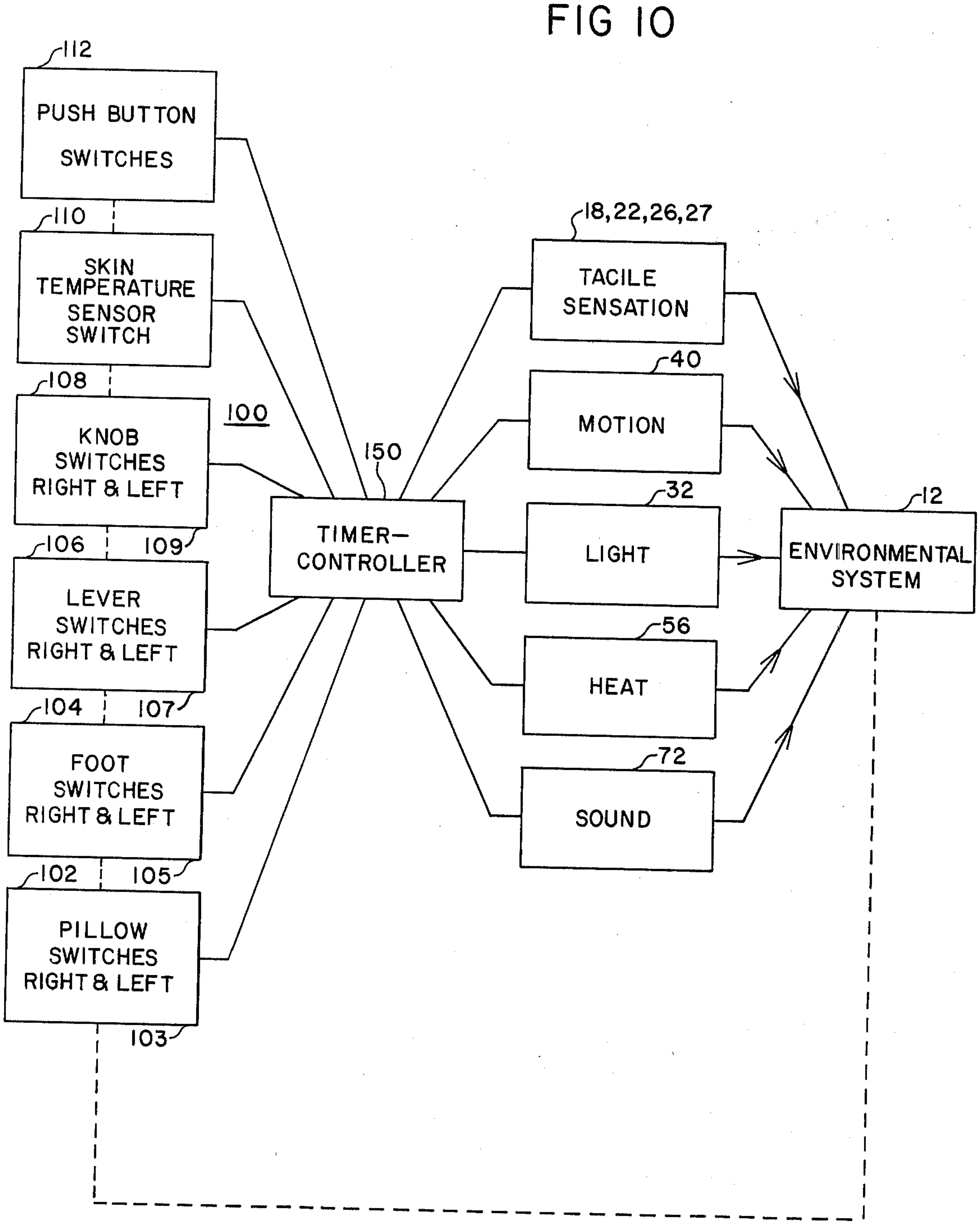

Referring now to FIG. 10, there is represented schematically a series of transducers 100 in the form of switches 102–112 positioned within the housing 12 such that they may be selectively operated by the infant. The switches 102–112 complete circuits to the timer-controller 150 which may be a microcomputer as explained above. The timer-controller 150 in response to the signals from transducers 100 causes the parameter generators, such as sling 18, bladder 22 and head and foot pillows 26 and 27 making up the tactile sensation generator, means 32 forming the light control generator, means 40 for generating motion, air and heat control mens 56, and acoustical generator 72, to be selectively activated. The switches 102 and 103 are right and left pillow switches operated by the infant turning its head or by head pressure and may be selectively utilized to instruct timer-controller 150 as to which parameters are to be modified and in which direction, up or down, more or less, etc. The switches 104 and 105 are right and left foot switches that can be operated by the infant's feet and instruct timer-controller 150 to modify another or a combination of parameters in accordance with a predetermined program in response to the infant's input. Switches 106 and 107 are right or left lever switches, switches 108 and 109 are right and left knob switches. Other types of switches, such as push button switches 116 and the like, may be positioned at the infant's comfortable reach or mounted in a control panel placed above the infant or on either side. In addition, sensors such as skin temperature switch 110, may be used to feed data to the timer-controller for action by the computer in accordance with a preselected program. For example the sound parameter could be turned on for a one to five minute period in response to the triggering of a specific switch 112 by the infant or later it could be programmed to turn on continuously until the infant activated switch 112 to turn it off.

The environment changes initiated by the infant can include the usual parameters such as sound, light, tactile sensation, temperature and motion and also the system could include colored lights, or moving displays or mobiles which could be added to function in conjunction with the other parameters. The system could also include a motorized bed which is movable like the upper torso portion of a hospital bed in response to infant controlled switches 112.

The timing mechanism could have means to generate multiple and variable patterns. For example: if the original non-infant operated control was scheduled to rock the system 10 minutes out of every 30 minutes on a fixed schedule, the infant control system might impose 1 to 5 minutes of additional rocking, during the 30 minute period, if the infant desired. Alternatively, the infant might be allowed to cancel the 10 minute rocking period if desired. The timer-controller 150 is designed such as to allow for limited and selective programming of a variety of environmental control possibilities of various difficulties as the infant matures and shows the capacity to invoke them. Each environmental parameter would be under separate control by the timer-controller 150 which control can be set or programmed to control each parameter for a selected time and mode in accordance with the infant accommodated. In like manner, the program can be up-dated and/or the control can be modular such that additional or different modular configurations can be added to or plugged into the basic system as the development of the infant progresses.

The environmental changes could vary from simple, immediate, small environmental modifications to more complex and variably delayed environmental effects to finally offering the infant essentially complete control of the variable portions of the control system, subject of course, to the safety limits imposed by the programmed timer-controller.

The system can, of course, be provided as a complete research unit with all of the variables multiply modifiable or provided with simpler fixed or taped programs of infant modifiable activities.

It should be apparent from the foregoing that preferred embodiments of the invention provide an apparatus and method which can initially simulate near term gravid intrauterine parameters and then provide for a selectable progressive transition of the infant from intrauterine to extrauterine environment under its control. It should be appreciated that the particular apparatus is illustrative of the preferred embodiment to provide the variable parameters but may, however, take many forms; and it is intended that the invention be restricted only by the scope of the appended claims. It should also be appreciated that further research may reveal that some sensory parameters are more important than others in which case the means to produce a specific sensation may be altered or even eliminated to keep the total device both simple and maximally effective.

What is claimed is:

1. An environmental transition system for infants operative to simulate the intrauterine environment sensed by the infant while in the uterus and selectively modify the simulated intrauterine environment over a period of time to an extrauterine environment sensed by the infant after it leaves the uterus comprising: a housing for receiving said infant upon delivery having means for supporting an infant therein, first respective means for generating in said housing at least four of the sensory environmental conditions of sound, temperature, tactile sensation, light and motion as sensed by the infant in its intrauterine environment, second respective means associated with said first respective means for selectively modifying one or more of said conditions from their initial values over a period of time to values substantially equal to those of an extrauterine environment and additional means responsive to the infant's movements or other responses to further modify one or more of said conditions in a limited and preselected manner.

2. An environmental transition system for infants operative to simulate the intrauterine environment sensed by the infant while in the uterus and selectively modify the simulated intrauterine environment over a period of time to an extrauterine environment sensed by the infant after it leaves the uterus comprising: a housing for receiving said infant upon delivery having means for supporting an infant therein, first respective means for generating in said housing at least three of the sensory environmental conditions of sound, temperature, tactile sensation, light and motion as sensed by the infant in its intrauterine environment, one of which is light, second respective means associated with said first respective means for selectively modifying one or more or said conditions from their initial values over a period of time to values substantially equal to those of an extrauterine environment and additional means responsive to the infant's movements or other responses to further modify one or more of said conditions in a limited and preselected manner.

3. An environmental transition system for infants operative to simulate the intrauterine environment sensed by the infant while in the uterus and selectively modify the simulated intrauterine environment over a period of time to an extrauterine environment sensed by the infant after it leaves the uterus comprising: a housing for receiving said infant upon delivery having means for supporting an infant therein, first respective means for generating in said housing at least three of the sensory environmental conditions of sound, temperature, tactile sensation, light and motion as sensed by the infant in its intrauterine environment, one of which is sound, said sound consisting of reproduced or simulated maternal cardiovascular and gut sounds as perceived by an intrauterine infant in late pregnancy, second respective means associated with said first respective means for selectively modifying one or more of said conditions from their initial values over a period of time to values substantially equal to those of an extrauterine environment and additional means responsive to the infant's movements or other responses to further modify one or more of said conditions in a limited and preselected manner.

4. An environmental transition system for infants operative to simulate the intrauterine environment sensed by the infant while in the uterus and selectively modify the simulated intrauterine environment over a period of time to an extrauterine environment sensed by the infant after it leaves the uterus comprising: a housing for receiving said infant upon delivery having means for supporting an infant therein, first respective means for generating in said housing at least three of the sensory environmental conditions of sound, temperature, tactile sensation, light and motion as sensed by the infant in its intrauterine environment, wherein one condition is tactile sensation, said tactile sensation being defined as a resileint, formfitting surface which is adaptable to engage upper and lower portions of the infant's body, second respective means associated with said first respective means for selectively modifying one or more of said conditions from their initial values over a period of time to values substantially equal to those of an extrauterine environment and additional means responsive to the infant's movements or other responses to further modify one or more of said conditions in a limited and preselected manner.

5. An environmental transition system for infants operative to simulate the intrauterine environment sensed by the infant while in the uterus and selectively modify the simulated intrauterine environment over a period of time to an extrauterine environment sensed by the infant after it leaves the uterus comprising: a housing for receiving said infant upon delivery having means for supporting an infant therein, first respective means for generating in said housing at least two of the sensory environmental conditions of sound, temperature, tactile sensation, light and motion as sensed by the infant in its intrauterine environment, wherein one condition is tactile sensation, said tactile sensation being defined as a resilient, formfitting surface which is adaptable to engage upper and lower portions of the infant's body, second respective means associated with said first respective means for selectively modifying one or more of said conditions from their initial values over a period of time to values substantially equal to those of an extrauterine environment and additional means responsive to the infant's movements or other responses to further modify one or more of said conditions in a limited and preselected manner.

6. An environmental transition system for infants operative to simulate the intrauterine environment sensed by the infant while in the uterus and selectively modify the simulated intrauterine environment over a period of time to an extrauterine environment sensed by the infant after it leaves the uterus comprising: a housing for receiving said infant upon delivery having means for supporting an infant therein, first respective means for generating in said housing at least two of the sensory environmental conditions of sound, temperature, tactile sensation, light and motion as sensed by the infant in its intrauterine environment, wherein one condition is sound, said sound consisting of reproduced or simulated maternal cardiovascular and gut sounds as perceived by an intrauterine infant in later pregnancy, second respective means associated with said first respective means for selectively modifying one or more of said conditions from their initial values over a period of time to values substantially equal to those of an extrauterine environment and additional means responsive to the infant's movements or other responses to further modify one or more of said conditions in a limited and preselected manner.

7. An environmental transition system for infants operative to simulate the intrauterine environment as sensed by the infant while in the uterus and selectively modify the simulated intrauterine environment over a period of time to an extrauterine environment sensed by the infant after it leaves the uterus comprising: a housing for receiving said infant upon delivery having means for supporting an infant therein, first respective means for generating in said housing at least two of the sensory environmental conditions of sound, temperature, tactile sensation, light and motion as sensed by the infant in its intrauterine environment, wherein one condition is light, said light including means to control ambient light entering the housing, second respective means associated with said first respective means for selectively modifying one or more of said conditions from their initial values over a period of time to values substantially equal to those of an extrauterine environment and additional means responsive to the infant's movements or other responses to further modify one or more of said conditions in a limited and preselected manner.

8. An environmental transition system for infants operative to simulate the intrauterine environment as sensed by the infant while in the uterus comprising: a housing for receiving said infant upon delivery having means for selectively generating in said housing at least four of the sensory environmental conditions of sound, temperature, tactile sensation, light and motion as sensed by the infant in is intrauterine environment, second respective means associated with said first respective means for selectively modifying the intrauterine-extrauterine transition environment, and additional means responsive to the infant's movements or other response to further modify one or more of said conditions in a limited and preselected manner.

9. The environmental transition system of claim 8 including means for gradually reducing over a period of time the exposure of said infant placed in the environmental transition system to said simulated intrauterine sensory environmental conditions to condition the infant to an extrauterine environment at an optimal rate.

10. The environmental transition system of claim 9 including means to vary at least one of either the intensity of said exposure or the time period of said exposure.

11. An environmental transition system for infants operative to simulate the intrauterine environment as sensed by the infant while in the uterus comprising: a housing for receiving said infant upon delivery having means for selectively generating in said housing at least three of the sensory environmental conditions of sound, temperature, tactile sensation, light and motion as sensed by the infant in its intrauterine environment, one of which is light, second respective means associated with said first respective means for selectively modifying the intrauterine-extrauterine transition environment, and additional means responsive to the infant's movements or other responses to further modify one or more of said conditions in a limited and preselected manner.

12. The environmental transition system of claim 11 including means for gradually reducing over a period of time the exposure of said infant placed in the environmental transition system to said simulated intrauterine sensory environmental conditions to condition the infant to an extrauterine environment at an optimal rate.

13. The environmental transition system of claim 12 including means to vary at least one of either the intensity of said exposure or the time period of said exposure.

14. An environmental transition system for infants operative to simulate the intrauterine environmental as sensed by the infant while in the uterus comprising: a housing for receiving said infant upon delivery having means for selectively generating in said housing at least three of the sensory environmental conditions of sound, temperature, tactile sensation, light and motion as sensed by the infant in its intrauterine environment, one of which is sound, said sound consisting of reproduced or simulated maternal cardiovascular and gut sounds as perceived by an intrauterine infant in late pregnancy, second respective means associated with said first respective means for selectively modifying the intrauterine-extrauterine transition environment, and additional means responsive to the infant's movements or other response to further modify one or more of said conditions in a limted and preselected manner.

15. The environmental transition system of claim 14 including means for gradually reducing over a period of time the exposure of said infant placed in the environmental transition system to said simulated intrauterine sensory environmental conditions to condition the infant to an extrauterine environment at an optimal rate.

16. The environmental transition system of claim 15 including means to vary at least one of either the intensity of said exposure or the time period of said exposure.

17. An environmental transition system for infants operative to simulate the intrauterine environment as sensed by the infant while in the uterus comprising: a housing for receiving said infant upon delivery having means for selectively generating in said housing at least three of the sensor environmental conditions of sound, temperture, tactile sensation, light and motion as sensed by the infant in is intrauterine environment, wherein one condition is tactile sensation, said tactile sensation being defined as a resilient, formfitting surface which is adaptable to engage upper and lower portions of the infant's body, second respective means associated with said first respective means for selectively modifying the intrauterine-extrauterine transition environment, and additional means responsive to the infant's movements or other responses to further modify one or more of said conditions in a limited and preselected manner.

18. The environmental transition system of claim 17 including means for gradually reducing over a period of time the exposure of said infant placed in the environmental transition system to said simulated intrauterine sensory environmental conditions to condition the infant to an extrauterine environment at an optimal rate.

19. The environmental transition system of claim 18 including means to vary at least one of either the intensity of said exposure or the time period of said exposure.

20. An environmental transition system for infants operative to simulate the intrauterine environment as sensed by the infant while in the uterus comprising: a housing for receiving said infant upon delivery having means for selectively generating in said housing at least two of the sensory environmental conditions of sound, temperature, tactile sensation, light and motion as sensed by the infant in its intrauterine environment, wherein one condition is tactile sensation, said tactile sensation being defined as a resilient, formfitting surface which is adaptable to engage upper and lower portions of the infant's body, second respective means associated with said first respective means for selectively modifying the intrauterine-extrauterine transition environment, and additional means responsive to the infant's movements or other response to further modify one or more of said conditions in a limited and preselected manner.

21. The environmental transition system of claim 20 including means for gradually reducing over a period of timme the exposure of said infant placed in the environmental transition system to said simulated intrauterine sensory environmental conditions to condition the infant to an extrauterine environment at an optimal rate.

22. The environmental transition system of claim 21 including means to vary at least one of either the intensity of said exposure or the time period of said exposure.

23. An environmental transition system for infants operative to simulate the intrauterine environment as sensed by the infant while in the uterus comprising: a housing for receiving said infant upon delivery having means for selectively generating in said housing at least two of the sensory environmental conditions of sound, temperature, tactile sensation, light and motion as sensed by the infant in its intrauterine environment, wherein one condition is light, said light including means to control ambient light entering the housing, second respective means associated with said first respective means for selectively modifying the intrauterine-extrauterine transition environment, and additional means responsive to the infant's movements or other responses to further modify one or more of said conditions in a limited and preselected manner.

24. The environmental transition system of claim 23 including means for gradually reducing over a period of time the exposure of said infant placed in the environmental transition system to said simulated intrauterine sensory environmental conditions to condition the infant to an extrauterine environment at an optimal rate.

25. The environmental transition system of claim 24 including means to vary at least one of either the intensity of said exposure or the time period of said exposure.

26. An environmental transition system for infants operative to simulate the intrauterine environment as sensed by the infant while in the uterus comprising: a housing for receiving said infant upon delivery having means for selectively generating in said housing at least two of the sensory environmental conditions of sound, temperature, tactile sensation, light and motion as sensed by the infant in its intrauterine environment, wherein one condition is sound, said sound consisting of produced or simulated maternal cardiovascular and gut sounds as perceived by an intrauterine infant in late pregnancy, second respective means associated with said first respective means for selectively modifying the intrauterine-extrauterine transition environment, and additional means responsive to the infant's movements or other responses to further modify one or more of said conditions in a limited and preselected manner.

27. The environmental transition system of claim 26 including means for gradually reducing over a period of time the exposure of said infant placed in the environmental transition system to said simulated intrauterine sensory environmental conditions to condition the infant to an extrauterine environment at an optimal rate.

28. The environmental transition system of claim 27 including means to vary at least one of either the intensity of said exposure or the time period of said exposure.

29. The method of transitioning an infant from intrauterine to extrauterine life by retaining the infant for a period of time under an optimum number of the conditions of sound, temperature, light, motion and tactile sensation simulating those same environmental conditions as sensed by the infant in the intrauterine environment, the method comprising:

a. providing a housing of internal size to receive and support the infant after delivery;
b. providing said housing with at least three of said sensory environmental conditions of sound, temperature, light, motion and tactile sensation;
c. transferring said infant to said housing after delivery; and
d. selectively conditioning said infant in said housing from the intrauterine to an extrauterine environment by selectively modifying over a period of time the time period or intensity or both to which said infant is exposed to said simulated intrauterine environmental conditions in said housing.

30. The method of claim 29 in which additional limited and selective modification of time and intensity of said environmental conditions is in response to an infant's movements and/or other responses.

31. The method of claim 29 in which one of said three sensory environmental conditions is light.

32. The method of claim 29 in which one of said three sensory environmental conditions is sound, said sound consisting of simulated maternal cardiovascular and gut sounds as perceived by an intrauterine infant in late pregnancy.

33. The method of claim 29 in which one of said three sensory environmental conditions is tactile sensation defined as a resilient, formfitting surface which is adaptable to engage upper and lower portions of the infant's body.

34. The method of transitioning an infant from intrauterine to extrauterine life by retaining the infant for a period of time under an optimum number of the conditions of sound, temperature, light, motion and tactile sensation simulating those same environmental conditions as sensed by the infant in the intrauterine environment, the method comprising:

a. providing a housing of internal size to receive and support the infant after delivery;
b. providing said housing with at least two of said sensory environmental conditions wherein one of said conditions is tactile sensation definedas a resilient, formfitting surface which is adaptable to engage upper and lower portions of the infant's body;
c. transferring said infant to said housing after delivery; and
d. selectively conditioning said infant in said housing from the intrauterine to an extrauterine environmental by selectively modifying over a period of time the time period or intensity or both to which said infant is exposed to said simulated intrauterine environmental conditions in said housing.

35. The method of claim 34 in which additional limited and selective modification of time and intensity of said environmental conditions is in response to an infant's movement and/or other responses.

36. The method of transitioning an infant from intrauterine to extrauterine life by retaining the infant for a period of time under an optimum number of the conditions of sound, temperature, light, motion and tactile sensation simulating those same environmental conditions as sensed by the infant in the intrauterine environment, the method comprising:

a. providing a housing of internal size to receive and support the infant after delivery;
b. providing said housing with at least two of said sensory environmental conditions, one of which is light, and including means to control ambient light entering the housing;
c. transferring said infant to said housing after delivery; and
d. selectively conditioning said infant in said housing from the intrauterine to an extrauterine environment by selectively modifying over a period of time the time period or intensity or both towhich said infant is exposed to said simulated intrauterine environmental conditions in said housing.

37. The method of claim 36 in which additional limited and selective modification of time and intensity of said environmenal conditions is in response to an infant's movements and/or other responses.

38. The method of transitioning an infant from intrauterine to extrauterine life by retaining the infant for a period of time under an optimum number of conditions of sound, temperature, light, motion and tactile sensation simulating those same environmental conditions as sensed by the infant in the intrauterine environment, the method comprising:

a. providing a housing of internal size to receive and support the infant after delivery;
b. providing said housing with at least two of said sensory environmental conditions, wherein one of said conditions is sound consisting of reproduced or simulated maternal cardiovascular and gut sounds as perceived by an intrauterine infant in late pregnancy;
c. transferring said infant to said housing after delivery; and
d. selectively conditioning said infant in said housing from the intrauterine to an extrauterine environment by selectively modifying over a period of time the time period or intensity or both to which said infant is exposed to said simulated intrauterine environmental conditions in said housing.

39. The method of claim 38 in which additional limited and selective modification of time and intensity of said environmental conditions is in response to an infant's movements and/or other responses.

* * * * *